(12) United States Patent
Grant et al.

(10) Patent No.: US 9,867,568 B1
(45) Date of Patent: Jan. 16, 2018

(54) SYSTEM AND METHOD OF MEASURING IN VIVO WEAR IN ARTIFICIAL KNEE JOINT

(71) Applicant: Caterpillar Inc., Peoria, IL (US)

(72) Inventors: Marion B. Grant, Princeville, IL (US); Nien L. Lee, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 27 days.

(21) Appl. No.: 15/192,733

(22) Filed: Jun. 24, 2016

(51) Int. Cl.
G06K 9/00 (2006.01)
A61B 5/00 (2006.01)
A61F 2/38 (2006.01)
A61B 6/03 (2006.01)
G06T 7/00 (2017.01)
G06T 7/60 (2017.01)

(52) U.S. Cl.
CPC ............ *A61B 5/4851* (2013.01); *A61B 6/032* (2013.01); *A61F 2/389* (2013.01); *A61F 2/3859* (2013.01); *A61F 2/3868* (2013.01); *G06T 7/0014* (2013.01); *G06T 7/602* (2013.01); *G06T 2207/10081* (2013.01); *G06T 2207/30052* (2013.01)

(58) Field of Classification Search
None
See application file for complete search history.

(56) References Cited

PUBLICATIONS

Magurie, Jr. et al. "A New Automated Way to Measure Polyethylene Wear in THA Using a High Resolution CT Scanner: Method and Analysis.", *The Scientific World Journal*, vol. 2014 (2014), Article ID 528407, 9 pages (Jan. 22, 2014).
Rahman et al., "Accurate Measurement of Three-Dimensional Natural Knee Kinematics Using Single Plane Flouroscopy", Summer Bioengineering Conference, Jun. 25-29, Sonesta Beach Resort, Key Biscayne, Florida, 2 pages (2003).

*Primary Examiner* — Atiba O Fitzpatrick
(74) *Attorney, Agent, or Firm* — Leydig, Voit & Mayer, LTD.

(57) ABSTRACT

A method of determining wear of an artificial knee assembly (AKA) includes acquiring a first set of computed tomography (CT) data about the AKA in vivo. A first volumetric file is generated based on the first set of CT data. A first point cloud data set is generated based on the first volumetric AKA file. A first dimensional analysis of the AKA is performed using the first point cloud data set. A second volumetric file is generated based on a second set of acquired CT data before implantation or from a model. A second point cloud data set is generated based on the second volumetric AKA file. A second dimensional analysis is performed using the second point cloud data set. The first dimensional analysis is compared to the second dimensional analysis and a determination is made if they are different from each other.

20 Claims, 6 Drawing Sheets

SYSTEM AND METHOD OF MEASURING IN VIVO WEAR IN ARTIFICIAL KNEE JOINT

TECHNICAL FIELD

This disclosure relates to orthopedic implants. In particular, the disclosure relates to systems and methods of measuring wear of artificial knee joint replacements in vivo.

BACKGROUND

Total joint arthroplasty is an operation involving the replacement of a damaged joint with an artificial joint in order to restore motion to the joint and function to the muscles and ligaments and other soft tissue structures that operate and control the joint.

The operation is typically performed on individuals with a painful, disabling arthritic joint that is no longer responsive to conservative treatment regimens. This operation typically entails implantation of two or more artificial joint members into respective natural joint members to replace deteriorated natural articulating surfaces with artificial equivalents.

Artificial joint assemblies have been devised for a variety of joints including hips, knees, ankles, shoulders, elbows, fingers, toes and wrists. While artificial joint components are designed to provide stable and permanent attachment to the natural adjacent body tissue(s), at attachment interfaces, over time, the artificial joint can relocate, loosen and/or wear, which can lead to a loss of function, bone deterioration and tissue debris generation. An increase in wear to the articulating surfaces of the artificial joint typically results in reduced function of the artificial joint and, in addition, produces joint debris, which are expelled from the joint area to the surrounding tissues and may cause adverse reactions in these tissues. As wear of a joint progresses and larger amount of particles are expelled to the surrounding tissues, further bone absorption and loosening of the joint implant may occur. Such loosening of a prosthetic joint implant and damage to surrounding tissues is often left undetected in a patient even if regularly checked by a physician.

Most modern methods currently employed for determining the extent of wear of an artificial joint rely on X-ray imaging, computer tomography, isotope bone scans, magnetic resonance and the like to image the implanted joint. Known methods are known to have insufficient accuracy or are technically difficult to perform and/or interpret, even by highly skilled professionals. Most modern joint replacement assemblies incorporate metal backed plastic components, metallic components, or ceramic components within metallic shells and the available imaging methods cannot produce sufficient resolution in order to determine artificial joint loosening and/or articulating surface wear.

As a result of inefficient detection methods, oftentimes the only indication of early joint loosening is the pain and discomfort suffered by the patient. Bone absorption may progress to a stage necessitating replacement surgery using larger implants, and/or bone grafts to accommodate for the lost bone tissue. The prognosis for success and service life of the implant after such a corrective operation is less predictable and depends, among other factors, on the extent of bone absorption suffered. If performed relatively early on, such corrective surgery has an increased chance of success. Therefore, a method capable of detecting the extent and depth of wear of the articulating surfaces of an artificial joint, or a method that is capable of detecting minute displacement of artificial joint components, is important both to the patient and the treating physician. Also, a more exact understanding of the condition of the components of numerous joints through their lives can facilitate faster improvements to joint design for better performance and longer life. Typical life of an artificial joint now is 15 to 20 years. With such high precision in vivo measurements, joint like may be able to be increased to 25 years and more in a matter of years of developments rather than over decades.

It will be appreciated that this background description has been created to aid the reader, and is not to be taken as an indication that any of the indicated problems were themselves appreciated in the art. While the described principles can, in some respects and embodiments, alleviate the problems inherent in other systems, it will be appreciated that the scope of the protected innovation is defined by the attached claims, and not by the ability of any disclosed feature to solve any specific problem noted herein.

SUMMARY

In one aspect, the present disclosure describes a method of determining wear of an artificial knee assembly, the method including acquiring a first set of computed tomography data about the artificial knee assembly in vivo. A first volumetric artificial knee assembly file is generated based on the first set of computer tomography data. A first point cloud data set is generated based on the first volumetric artificial knee assembly file. A first dimensional analysis of the artificial knee assembly is performed using the first point cloud data set. A second volumetric artificial knee assembly file is generated based on a second set of acquired computed tomography data about the artificial knee assembly before implantation or acquiring the second volumetric artificial knee assembly file from a model. A second point cloud data set is generated based on the second volumetric artificial knee assembly file. A second dimensional analysis is performed using the second point cloud data set. The first dimensional analysis is compared to the second dimensional analysis. A determination is made if the first dimensional analysis is different from the second dimensional analysis an amount that exceeds a selected tolerance of the artificial knee assembly.

In another aspect, a system is disclosed for determining wear of an artificial knee assembly, including a CT x-ray machine configured to scan an artificial knee assembly in vivo and a computer system in communication with the CT x-ray machine. The computer system is configured to acquire a first set of computed tomography data about the artificial knee assembly in vivo, generate a first volumetric artificial knee assembly file based on the first set of computer tomography data, generate a first point cloud data set based on the first volumetric artificial knee assembly file and perform a first dimensional analysis of the artificial knee assembly using the first point cloud data set. The computer system is further configured to at least one of generate a second volumetric artificial knee assembly file based on a second set of acquired computed tomography data about the artificial knee assembly before implantation or acquire the second volumetric artificial knee assembly file from a model, generate a second point cloud data set based on the second volumetric artificial knee assembly file, perform a second dimensional analysis using the second point cloud data set, compare the first dimensional analysis to the second dimensional analysis, and determine if the first dimensional analysis is different from the second dimensional analysis an amount that exceeds a selected tolerance of the artificial knee assembly.

Further and alternative aspects and features of the disclosed principles will be appreciated from the following detailed description and the accompanying drawings. As will be appreciated, the principles related to determining wear of artificial joints as disclosed herein are capable of being carried out in other and different embodiments, and capable of being modified in various respects. Accordingly, it is to be understood that both the foregoing general description and the following detailed description are exemplary and explanatory only and do not restrict the scope of the appended claims.

DETAILED DESCRIPTION

Figure 1:
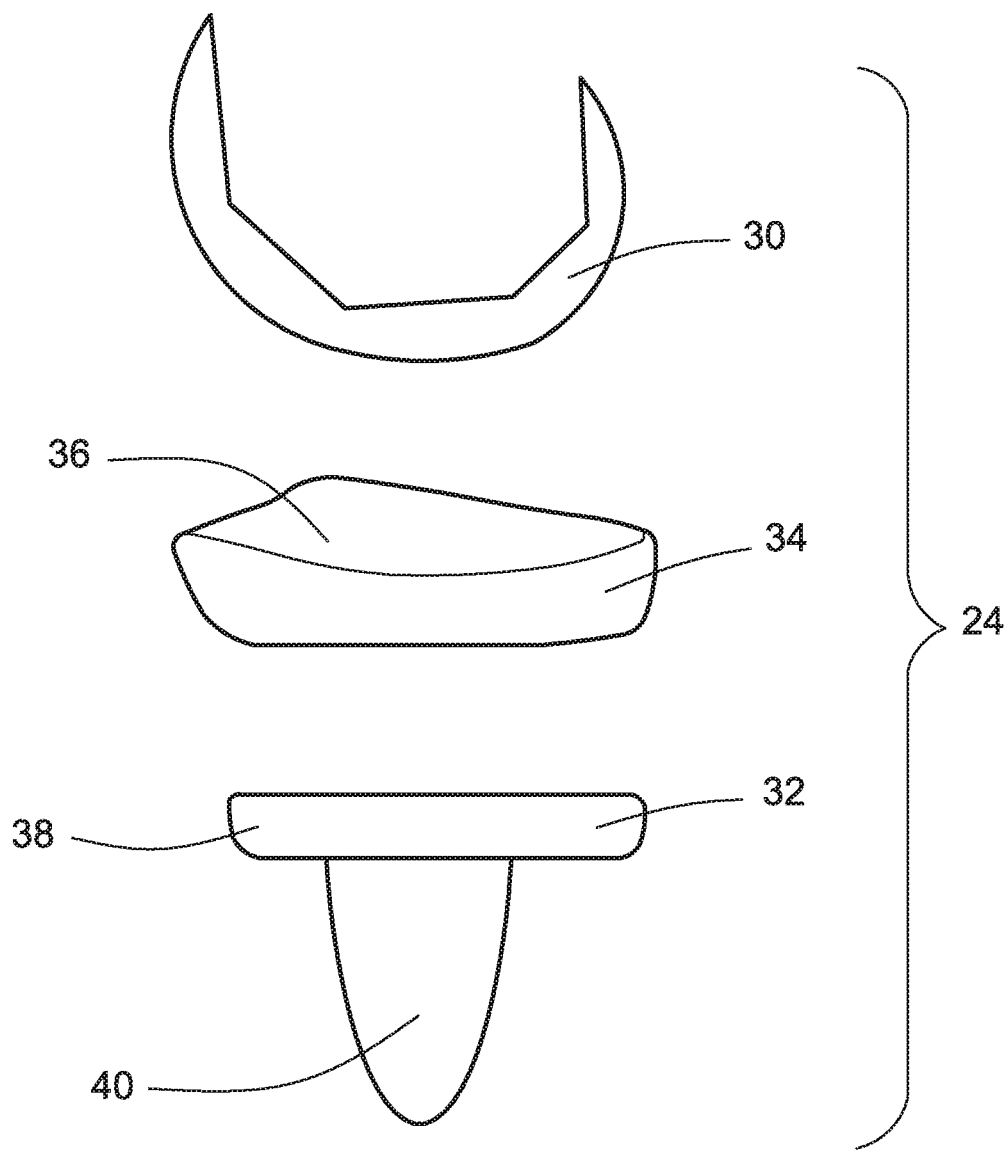
FIG. 1 is an expanded view of an embodiment of an artificial joint assembly.

FIG. 1 shows an exploded view of a conventional artificial knee joint assembly 24 including a femoral component 30, a tibial tray 32, and a spacer or insert plate 34 positioned between the femoral component 30 and the tibial tray 32. The femoral component 30 is a rounded, cup-shaped component that may be made of metallic or ceramic materials. The insert plate 34 includes an upper slide surface 36, which is shaped and sized to movably receive the femoral component 30. The slide surface 36 permits articulation of the femoral component 30 on the insert plate 34 while supporting the motion of the femoral component by discouraging misalignment or displacement of the components. For clarity, a patellar component is not shown in this disclosure.

The insert plate 34 may be made of any suitable bearing material such as polyethylene. An upper surface or tray part 38 of the tibial tray 32 receives the insert plate 34. The tibial tray 32 also includes an anchor part 40 extending from the tray part and may be made of metallic or ceramic materials.

Figure 2:
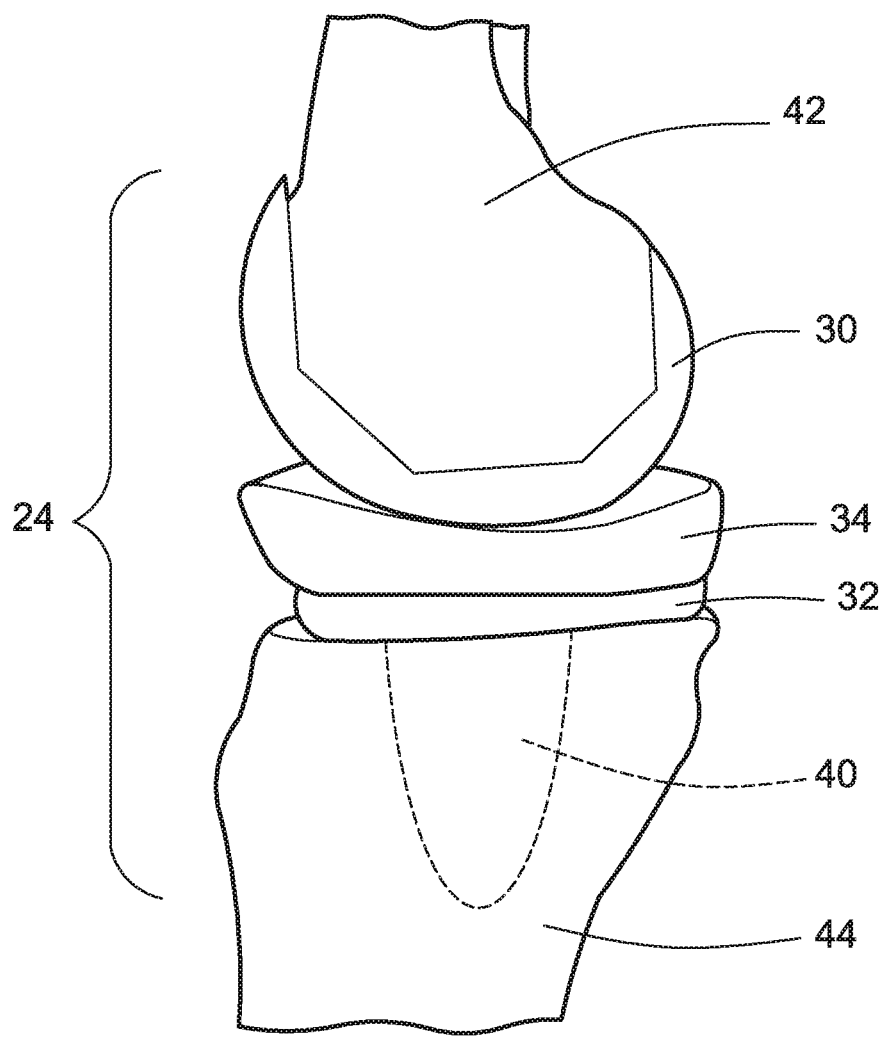
FIG. 2 is a front view of the artificial joint assembly of FIG. 1 in vivo.

FIG. 2 shows the artificial knee joint assembly 24 in vivo, with the soft tissue omitted for clarity, and with the femoral component 30 fixed onto a distal portion of a femur 42. The tibial tray 32 is fixed onto a proximal portion of a tibia 44 via the anchor part 40. The insert plate 34 is positioned onto the upper surface 38 of the tibial tray 32 to movably receive the femoral component 30 thereon. It will be understood that all configurations and variations of an artificial knee joint assembly 24 are contemplated by the present disclosure.

In a conventional artificial knee joint 24, an insert plate 34 of the tibial component 32 is typically formed from ultra-high molecular weight polyethylene (UHMWPE). The insert plate wears, albeit slightly, since it slides in contact with the femoral component 30 that is made of a metal or ceramics. It has been known that the insert plate 34 becomes thinner through use over a period of time after being implanted in a human body. Therefore, it is a common practice to design the insert plate 34 with a predetermined thickness (normally from about 2 to 5 mm) and taking the wear loss into account.

Since the slide surface 36 of the insert plate 34 is normally a concave surface that is recessed from the uppermost extent of the insert plate, the overall thickness of the insert plate must be made larger than the above-mentioned predetermined thickness to ensure sufficient thickness of the sliding surface.

The wear of the insert plate 34 can cause various problems for the user and can eventually lead to deterioration of the performance of the joint. At some point, it may become necessary to replace at least the insert plate 34. The point at which some or all components of the artificial joint assembly 24 should be replaced is before a critical, predetermined wear threshold is exceeded. Timing of replacement may take into account several factors, including but not limited to medical indications, manufacturers recommendations regarding specified wear amounts, and patient symptoms. For purposes of the present disclosure, the point at which one or more component of the artificial joint assembly 24 should be replaced, typically the insert plate 34 may be referred to as a selected tolerance.

Figure 4:
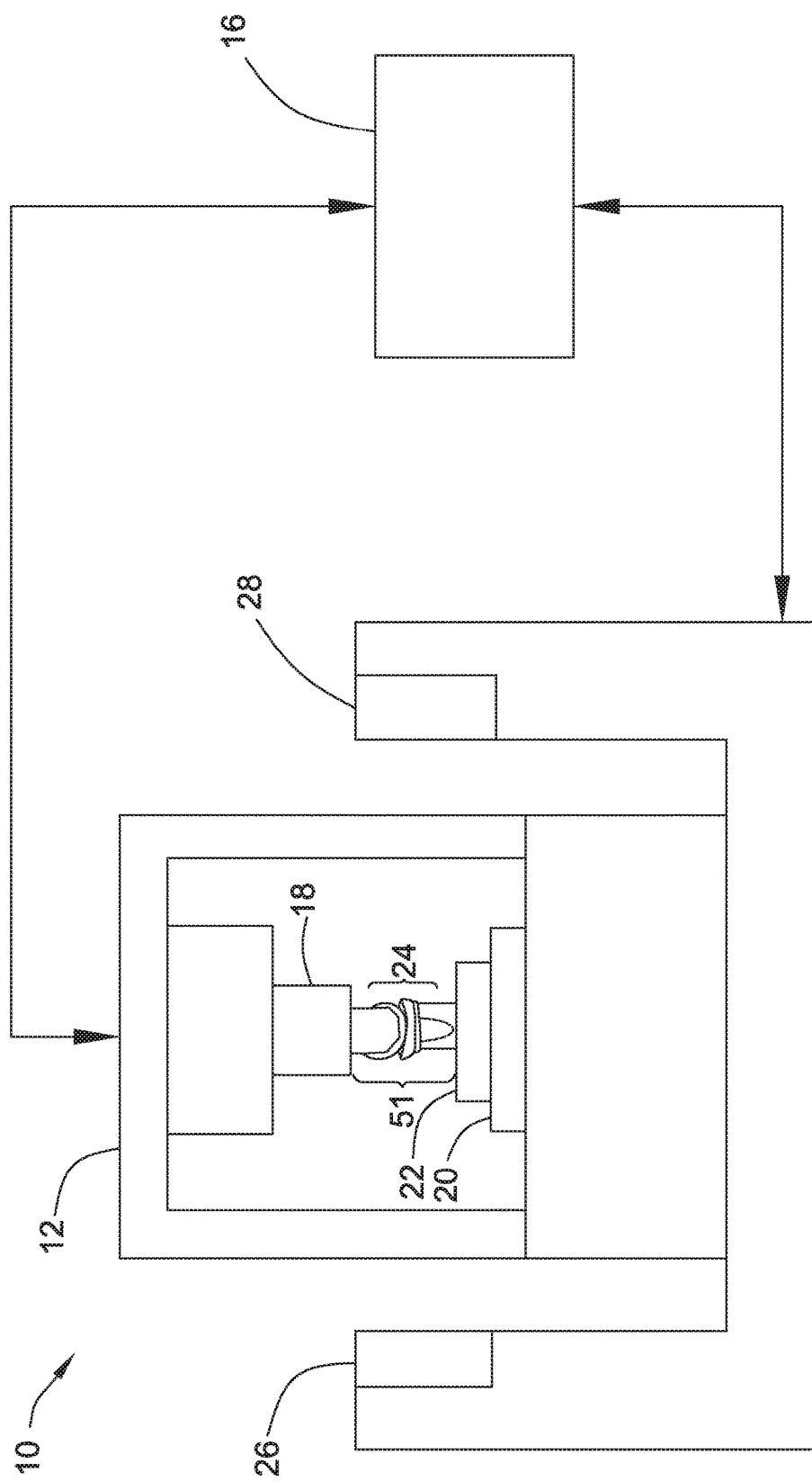
FIG. 4 is an embodiment of a system of measuring the initial, pre-implanted dimensions of an artificial knee joint assembly.

FIG. 4 illustrates an embodiment of a system 10 for measuring the initial dimensions of an artificial knee joint assembly, i.e., for measuring the assembled artificial joint assembly before implantation into a patient. The system 10 may include an artificial joint assembly holding apparatus 12, a computed tomography (CT) x-ray machine 14, and a computer 16.

In general, CT x-ray machine 14 may be configured to obtain data from imaging artificial knee joint assembly 24 disposed on the joint holding apparatus 12, while computer 16 may be configured to analyze the data acquired from scanning the artificial knee joint assembly 24. The computer 16 also may be used to store the analysis for comparison with a CT x-ray scan and analysis of the same artificial knee joint assembly 24 after implantation (FIG. 5), i.e., in vivo.

Joint holding apparatus 12 may be any type of elements, machines or a system of elements or machines suitable for holding the artificial knee joint assembly 24 for scanning by the CT x-ray machine 14. Alternatively, the joint holding apparatus 12 is also configured to apply a selected load on the joint assembly 24 while it is being scanned. In alternate embodiments, the load may be zero or a selected, predetermined load, for example, body weight of the patient.

Figure 3:
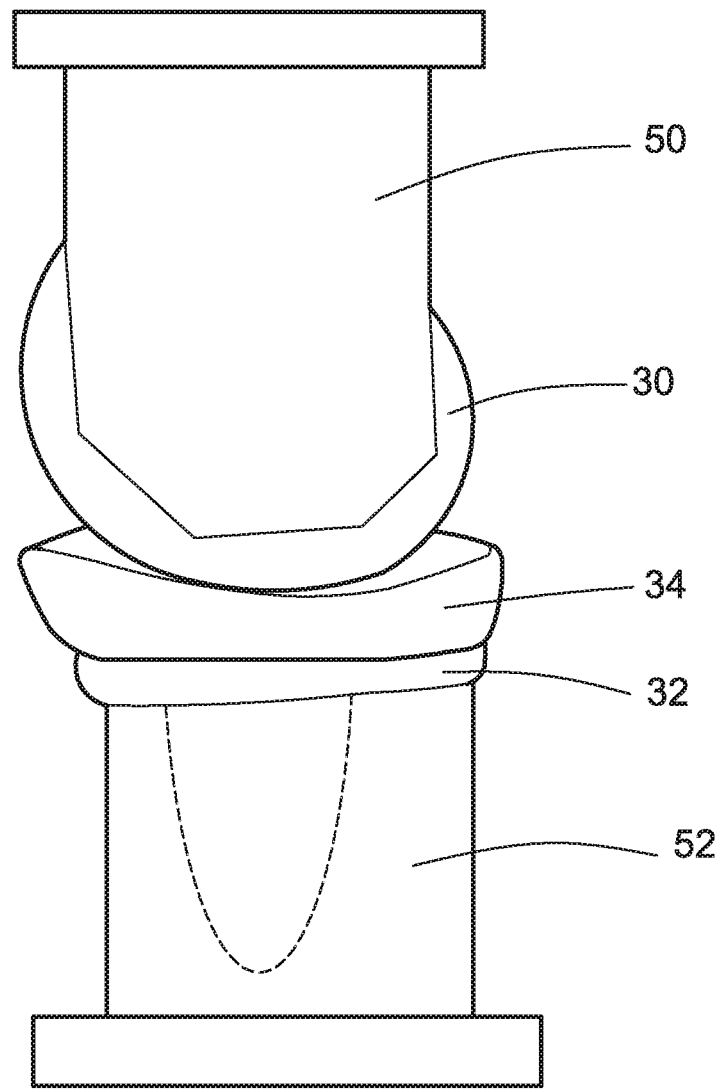
FIG. 3 is a front view of the artificial joint assembly in a holding fixture.

Referring to FIGS. 3 and 4, joint holding apparatus 12 includes a femoral component fixture 50 and a tibial tray fixture 52 that comprise a joint assembly-holding fixture 51. The femoral component fixture 50 has a shape and size to receive and attach to the femoral component 30. The tibial tray fixture 52 has a shape and size to receive and attach to the tibial tray 32.

When the joint holding apparatus 12 is being employed to hold the artificial knee joint assembly 24, the insert plate 34 is disposed between the femoral component 30 and the tibial tray 32 such that the artificial knee joint assembly 24 is assembled into an anatomically correct and operable state. The femoral component fixture 50 and tibial tray fixture 52 are both mountable to the joint holding apparatus 12 by any suitable structure and method, including the use of fasteners, such as bolts.

The joint holding apparatus 12 includes a base 22 to which the tibial tray fixture 52 is attachable and an optional load measuring system 20 upon which the base 22 is mounted. The joint holding apparatus 12 includes a load-applying system 18 to which the femoral component fixture 50 is attachable. The joint holding apparatus 12 can include an Instron® type system or a similar variable load application system. The joint holding apparatus 12 may be rotatable to provide the CT x-ray system 14 with a plurality of positions for scanning necessary for computed tomography methodology. Alternatively, some of the components of the CT x-ray system 14 can be rotated and the joint holding apparatus 12 can be held stationary.

The joint holding apparatus 12 is operably associated with a CT x-ray system 14. The joint holding apparatus 12 is configured to hold the joint assembly 24 so as to be scanned by the CT x-ray system 14. The CT x-ray system 14 can include any suitable x-ray scanner that is capable of scanning the joint assembly 24 when held by the holding apparatus 12 and obtaining sufficient quality and amounts of data to accurately image and measure the joint assembly.

CT x-ray machine 14 may by any type of machine suitable for performing high-resolution, three-dimensional imaging of artificial knee assembly 24. As illustrated in FIG. 4, CT x-ray machine 14 includes a radiation emitter 26 and a radiation detector 28. In one embodiment, radiation emitter 26 and radiation detector 28 may be fixed relative to artificial knee assembly 24. In another embodiment, radiation emitter 26 and radiation detector 28 may be configured to rotate, for example, about 360 degrees around artificial knee assembly 24 (i.e., around a vertical, horizontal or selected axis passing through artificial knee assembly 24). Radiation emitter 26 may include any suitable type of x-ray tube, such as for example, a 100-500 kV, high-power or micro-focus x-ray tube. Moreover, radiation emitter 26 may include a plurality of radiation tubes, or sources. Radiation detector 28 may be a digital detector configured to detect radiation emitted from radiation emitter 26, as affected by the geometry of artificial knee assembly 24. For example, radiation detector 28 may include a 1-10 megapixel digital radiation detecting mechanism. In one embodiment, radiation detector 28 may include an array, or plurality, of digital detectors configured to cooperate with corresponding radiation emitters 26. CT x-ray machine 14 may include a built-in processor 16 configured to control the operation of radiation emitter 26 and/or radiation detector 28. CT x-ray machine may also include built-in processing for data storage, component feature extraction, volume reconstruction, rendering/visualization, dimensional analysis, and/or performing comparisons. In one embodiment, CT x-ray machine 14 may further include a built-in display monitor for displaying three-dimensional representations of components. In another embodiment, the artificial joint assembly 24 is positioned closer to the radiation emitter 26 than the radiation detector 28 to create a magnification effect based on the ratio of the distance of the artificial knee assembly divided by the distance of the artificial knee assembly to the radiation detector.

The computer 16 may be integral with the CT x-ray system 14 or separate and in communication with the CT x-ray system. Computer 16 may include a single microprocessor or multiple microprocessors that include control mechanisms to operate CT x-ray machine 14. Numerous commercially available microprocessors may perform the functions of computer 16. It should be appreciated that computer 16 could readily embody a general machine microprocessor capable of controlling numerous machine functions. Computer 16 may include or be associated with a memory for storing data such as for example, an operating condition, a design limit, and a performance characteristic or specification of CT x-ray machine 14, and/or model artificial knee assemblies and actual artificial knee assemblies 24. Various other known circuits may be associated with computer 16, including power supply circuitry, signal-conditioning circuitry, solenoid driver circuitry, communication circuitry, and other appropriate circuitry. Moreover, because computer 16 may communicate with other components via either wired or wireless transmission, computer 16 may be disposed in a location remote from CT x-ray machine 14, if desired. Alternatively, as discussed above, computer 16 may be integral with CT x-ray machine 14. Accordingly, computer 16 may be configured to receive signals from CT x-ray machine 14 including CT data about the geometry of the artificial knee assembly 24. Computer 16 may be configured to store, analyze and compare the CT data and send reports, images, alerts, and other information based on the raw or analyzed CT data.

Figure 5:
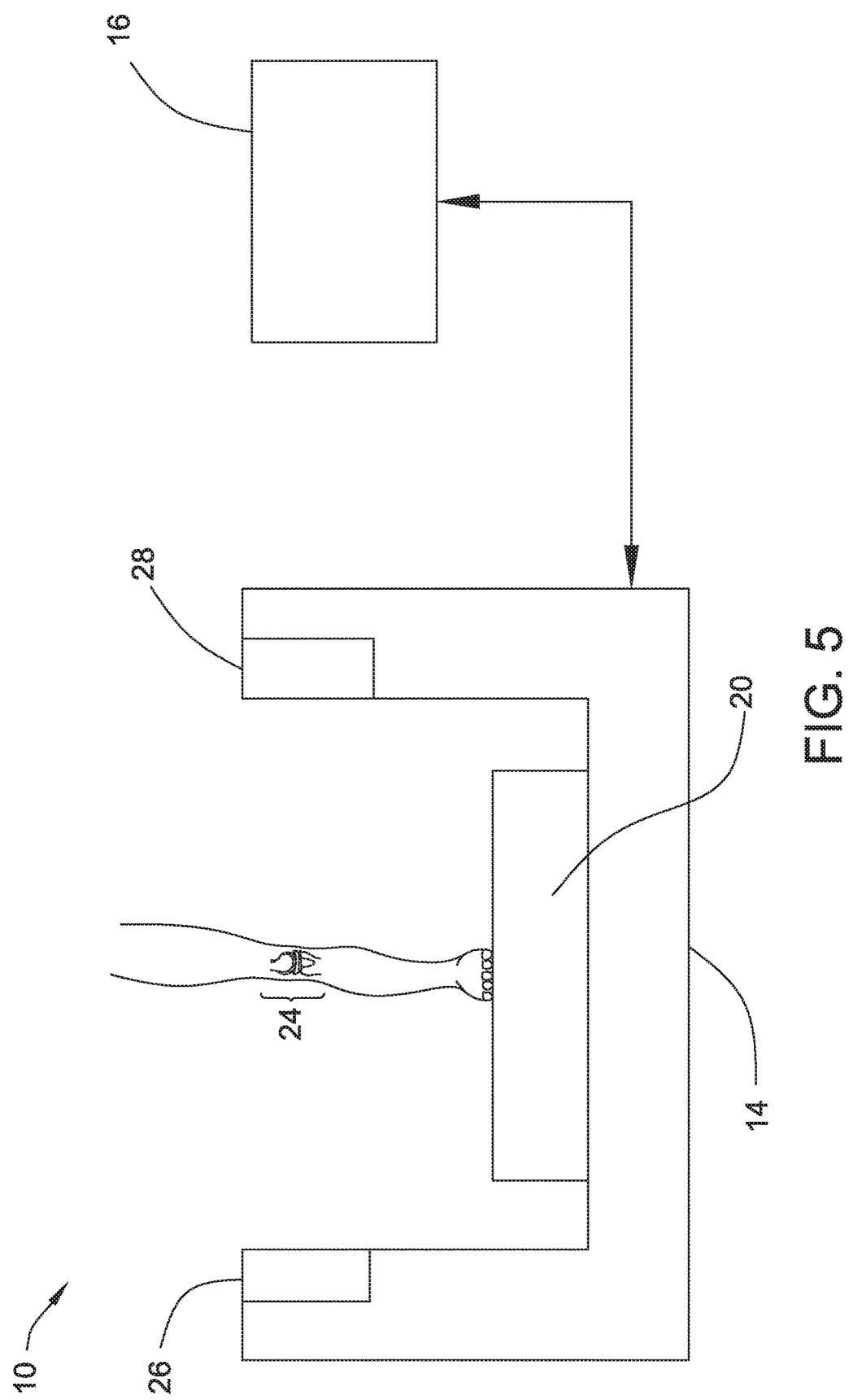
FIG. 5 is an embodiment of a system of measuring the dimensions of an artificial knee joint assembly in vivo.
Figure 6:
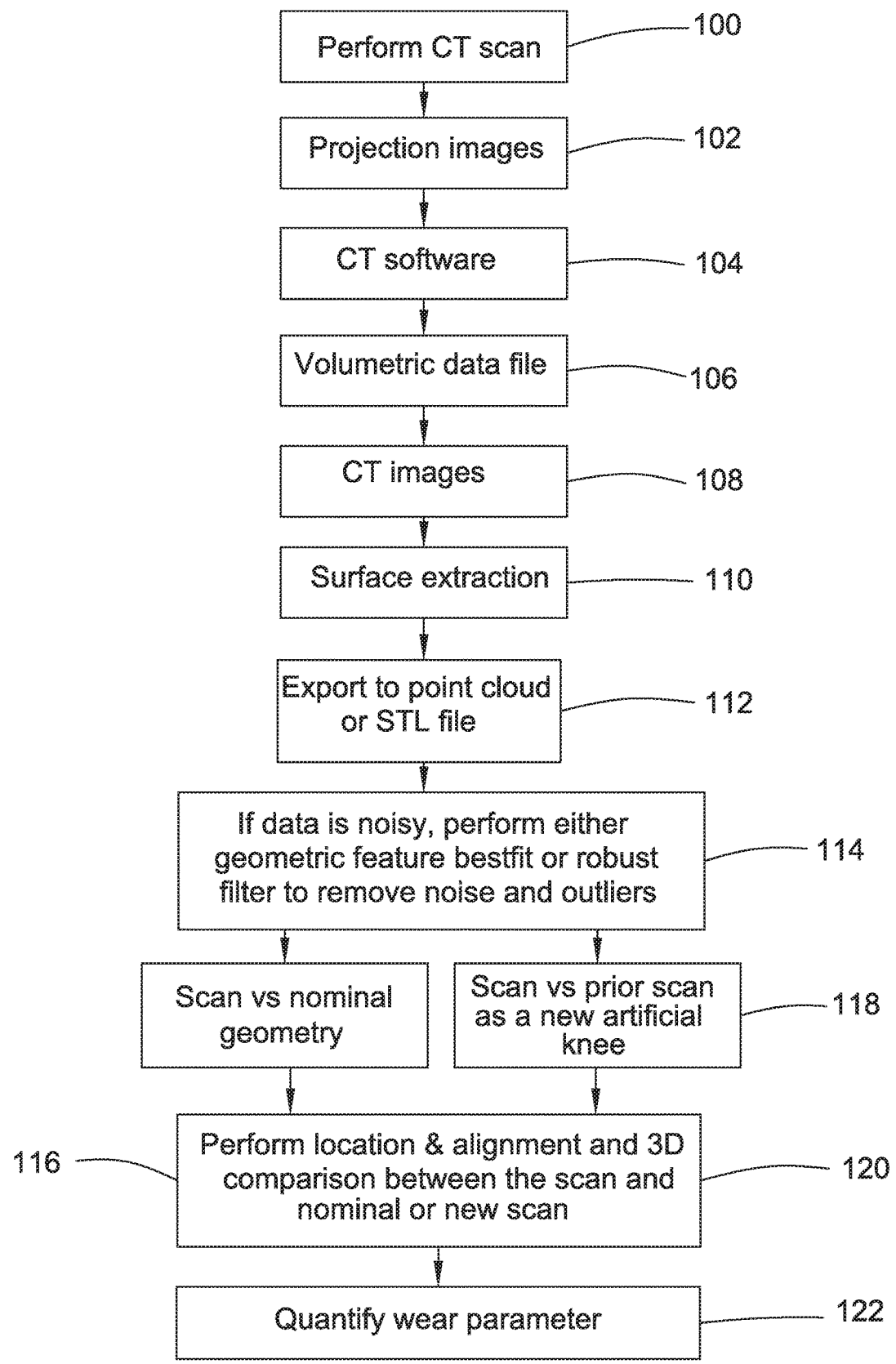
FIG. 6 is a flowchart illustrating an embodiment of a method of determining wear of an artificial knee assembly.

Referring to FIG. 5, CT x-ray machine 14 may perform the same operations as in the configuration shown in FIG. 4, but of an in vivo artificial knee assembly 24. Specifically, the system 10 includes a CT x-ray machine 14 with an x-ray emitter 26 and an x-ray detector 28 arranged as in the device shown in FIG. 4. Also, a computer 16 is provided in communication with the CT x-ray machine 14 for receiving the data from the CT x-ray machine, performing storage and computational operations and generating outputs from scanning the artificial knee assembly 24 in vivo. It will be understood that the same operations are performed on the artificial knee assembly 24 that were undertaken during the initial or first imaging and analysis process. The CT x-ray machine 14 includes a base 20 that also may include a load cell. In one embodiment of the disclosure, the load on the artificial knee assembly 24 in vivo is made to be the same as during the initial imaging and analysis process. Loading the artificial knee assembly 24 the same in both processes, i) initially and, ii) in vivo, may ensure consistency of results and a reliable comparison. Tests may be performed with the artificial knee assembly 24 pre-implantation and in vivo with zero load or with a selected load applied to the assembly, such as equal to body weight of the patient or a selected suitable load.

In operation, CT x-ray machine 14 may acquire computed tomography data about the geometry of a particular artificial knee assembly 24 before implantation (step 100) by performing a scan of the artificial knee assembly. Alternatively, a reference data set may be acquired from a computer file or digitized 3D image in a suitable format of a model and/or reference artificial knee assembly, which will form the basis for comparison between the reference artificial knee assembly and the particular artificial knee assembly in vivo. For example, the model may be supplied by the manufacturer and may represent an ideal, unworn artificial knee assembly 24.

To acquire data of an artificial knee assembly 24, base 20 may intermittently rotate artificial knee assembly by 360 degrees, in half-degree increments, for example, about an axis. CT x-ray machine 14 may use radiation emitter 26 and radiation detector 28 to generate a cross-sectional artificial knee assembly image corresponding to each of the half-degree increments. Accordingly, CT x-ray machine 14 may generate 720 projection images, or "slices," of artificial knee assembly 24, each image being a two-dimensional representation of the features of artificial knee assembly 24 across a particular, rotationally-oriented plane (step 102). The number of images acquired in order to obtain a sufficiently detailed data set may be specified based upon the resolution of the detector.

The projection images are processed by standard CT software (step 104) associated with either CT x-ray machine 14 or computer 16 to generate a volumetric artificial knee assembly data file representing the physical characteristics of artificial knee assembly 24 (step 106). Specifically, CT x-ray machine 14 may communicate the acquired CT data to computer 16, to be assembled into a three-dimensional, volumetric artificial knee assembly data file. Alternatively, the volumetric artificial knee assembly data file may be generated by a processor built-in to CT x-ray machine 14. From the volumetric artificial knee assembly file cross sections of the artificial knee assembly may be obtained in a conversion process from the volumetric artificial knee assembly file (step 108).

A process to extract the surface of the scanned components is conducted (step 110). The surface extraction process may include beam hardening correction and/or localized corrected edge detection, both of which are known correction processes.

Either CT x-ray machine 14 or computer 16 may then generate point cloud data from the volumetric artificial knee assembly data file (step 112). Specifically, the volumetric artificial knee assembly file may be converted into point cloud data by various statistical and geometrical methods, with each data point in the cloud representing an approximate location of a point on one of the metal or ceramic surfaces of the artificial knee assembly 24. A point cloud is a set of data points in a coordinate system. In a three-dimensional coordinate system, these points are usually defined by X, Y, and Z coordinates, and often are intended to represent the external surface of an object. The CT x-ray machine 14 measures a large number of points on an object's surface, and often output a point cloud as a data file. The point cloud represents the set of points that the device has measured. The generation of the point cloud data may be performed by commercially available software, for example Siemens Imageware™, Innometric Polyworks™, 3D Systems Geomagic™, GOM Inspect, Hexagon PC-DMIS Reshaper, or Volume Graphic Studio™. The point cloud data may be exported to a STL file, which is a file format native to a brand of stereolithography CAD software, or a similar mesh handling.

For example, each of the femoral component 30 and the tibial component 32 may be represented by approximately at least 100,000 data points defining a geometry of each component and a space therebetween that is occupied by the insert plate 34, thereby defining the critical geometry of the insert plate. Even in the event that a selected type of CT x-ray machine 14 only obtains each data point to 6 or 7 um, the analysis of thousands of neighboring data points may be used to improve the imaging resolution to the micron level. For example, statistical averages and probabilities may be used to optimize an approximated location for a data point. Accordingly, the geometry of each of the femoral component 30 and the tibial component 32, and even the insert plate 34 of the artificial knee assembly 24, may be determined to a resolution as low as 3-5 um.

If the point cloud data is noisy, the noise may be removed according to any well-known process such as the use of a best fit process, wherein the data is compared to known geometric configurations, such as planes, spheres, cones, cylinders, and so on. Alternatively, or in addition, the data may be filtered with a robust filter (step 114) based on, for example, spline filtering.

There are two options for analyzing the wear or change of dimensions of a subject in vivo artificial knee assembly. The subject in vivo artificial knee assembly 24 may be compared to a reference standard artificial knee assembly (step 116) or alternatively, the subject in vivo artificial knee assembly may be compared to the same artificial knee assembly scanned before implantation (step 118). The subject in vivo artificial knee assembly 24 may be scanned, analyzed and compared to a reference or the pre-implanted assembly at selected time intervals so as to monitor the wear of components of the assembly over time.

The subject in vivo artificial knee assembly 24 is subjected to location and alignment procedures to perform a 3D comparison with the reference or the pre-implanted assembly (step 120). Differences between the reference or the pre-implanted assembly to the subject in vivo artificial knee assembly are quantified (step 122). The quantified differences are used to determine if the subject in vivo artificial knee assembly 24 exceeds a selected wear tolerance. If it is found that the wear tolerance has been exceeded, a decision can be made to replace the worn component.

The above-described steps of: generating the volumetric artificial knee assembly file, generating the point cloud data, and performing dimensional analysis may be performed within CT x-ray machine 14 or by computer 16. Alternatively, each step may be performed on a separate computer 16, separate processor, and/or a separate software package, in a so-called "parallel processing" or "pipe-lining" process. Because the processing steps may be divided across distinct computers, processors, and/or software suites, the processing of data in these steps may be expedited to a pace that may make possible the real time imaging of artificial knee assembly 24. Full processing from imaging to 3D construction results can be accomplished in 10 minutes or less. Geometric dimensional analysis can then be performed after this under 10 minute data acquisition step.

INDUSTRIAL APPLICABILITY

The present disclosure is applicable to monitoring wear in an artificial joint, such as an artificial knee assembly in vivo. The subject in vivo knee assembly can be scanned and the assembly analyzed to acquire a point cloud data set that is comparable to a reference artificial knee assembly or the actual implanted knee assembly scanned before implantation. Wear of the knee assembly can be monitored over time and determined to a highly accurate degree.

It will be appreciated that the foregoing description provides examples of the disclosed system and method. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method of determining wear of an artificial knee assembly, the method comprising:
   acquiring a first set of computed tomography data about the artificial knee assembly in vivo;
   generating a first volumetric artificial knee assembly file based on the first set of computed tomography data;

generating a first point cloud data set based on the first volumetric artificial knee assembly file;
performing a first dimensional analysis of the artificial knee assembly using the first point cloud data set;
generating a second volumetric artificial knee assembly file based on a second set of acquired computed tomography data about the artificial knee assembly before implantation or acquiring the second volumetric artificial knee assembly file from a model;
generating a second point cloud data set based on the second volumetric artificial knee assembly file;
performing a second dimensional analysis using the second point cloud data set;
comparing the first dimensional analysis to the second dimensional analysis; and
determining if the first dimensional analysis is different from the second dimensional analysis an amount that exceeds a selected tolerance of the artificial knee assembly.

2. The method of claim 1, comprising performing surface extraction preceding the generation of each of generation of the first and second point cloud data sets.

3. The method of claim 1, wherein noise reduction is performed on at least the first point cloud data set.

4. The method of claim 3, wherein noise reduction is performed on the first point cloud data set and the second point cloud data set.

5. The method of claim 3, wherein the noise reduction includes at least one of performing a geometric feature best fit process and applying a robust filter.

6. The method of claim 1, wherein first set of computed tomography data is acquired with a selected load applied to the artificial knee assembly.

7. The method of claim 6, wherein the selected load is zero.

8. The method of claim 6, wherein the selected load is bodyweight.

9. The method of claim 6, wherein the second set of computed tomography data is acquired with the selected load being the same as that used in acquiring the first set of computed tomography data.

10. The method of claim 1, wherein the first dimensional analysis determines the dimensions of an insert plate of the artificial knee assembly in vivo.

11. The method of claim 10, wherein the second dimensional analysis determines the dimensions of the insert plate of the artificial knee assembly before implantation.

12. The method of claim 10, wherein the second dimensional analysis determines the dimensions of an insert plate of a model artificial knee assembly.

13. A system for determining wear of an artificial knee assembly, comprising:
a CT x-ray machine configured to scan an artificial knee assembly in vivo; and
a computer system in communication with the CT x-ray machine, the computer system configured to acquire a first set of computed tomography data about the artificial knee assembly in vivo, generate a first volumetric artificial knee assembly file based on the first set of computed tomography data, generate a first point cloud data set based on the first volumetric artificial knee assembly file; and perform a first dimensional analysis of the artificial knee assembly using the first point cloud data set;
wherein the computer system is further configured to at least one of generate a second volumetric artificial knee assembly file based on a second set of acquired computed tomography data about the artificial knee assembly before implantation or acquire the second volumetric artificial knee assembly file from a model, generate a second point cloud data set based on the second volumetric artificial knee assembly file, perform a second dimensional analysis using the second point cloud data set, compare the first dimensional analysis to the second dimensional analysis, and determine if the first dimensional analysis is different from the second dimensional analysis an amount that exceeds a selected tolerance of the artificial knee assembly.

14. The system of claim 13, further comprising an artificial joint holding apparatus configured to hold the artificial knee assembly in a position suitable for the CT x-ray machine to scan the artificial knee assembly.

15. The system of claim 14, wherein the artificial joint holding apparatus includes a femoral component fixture shaped and sized to hold a femoral component of the artificial knee assembly and a tibial tray component fixture shaped and sized to hold a tibial tray component of the artificial knee assembly.

16. The system of claim 14, further comprising a load applying machine connected to the artificial joint holding apparatus, the load applying machine configured to apply a selected load on the artificial knee assembly for scanning.

17. The system of claim 16, wherein the load applying machine is configured to apply a load on the artificial knee assembly before implantation.

18. The system of claim 17, wherein the load applying machine is configured to apply a load on the artificial knee assembly before implantation from zero to about body weight.

19. The system of claim 17, wherein the load applying machine is configured to apply a load on the artificial knee assembly in vivo.

20. The system of claim 19, wherein the load applying machine is configured to apply a load on the artificial knee assembly in vivo from zero to about body weight.

* * * * *